United States Patent
Li et al.

(10) Patent No.: US 7,675,037 B2
(45) Date of Patent: Mar. 9, 2010

(54) METHOD AND APPARATUS FOR MEASURING TERAHERTZ TIME-DOMAIN SPECTROSCOPY

(75) Inventors: Yuanjing Li, Beijing (CN); Bing Feng, Beijing (CN); Ziran Zhao, Beijing (CN); Yingxin Wang, Beijing (CN); Dongmei Yu, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 92 days.

(21) Appl. No.: 11/964,363

(22) Filed: Dec. 26, 2007

(65) Prior Publication Data

US 2008/0157750 A1 Jul. 3, 2008

(30) Foreign Application Priority Data

Dec. 31, 2006 (CN) .................... 2006 1 0171670

(51) Int. Cl.
*G01J 5/02* (2006.01)
(52) U.S. Cl. .................................................. 250/341.1
(58) Field of Classification Search ............... 250/341.1
See application file for complete search history.

(56) References Cited

U.S. PATENT DOCUMENTS 4,446,557 A * 5/1984 Figueroa .................. 372/45.01
6,208,458 B1 * 3/2001 Galvanauskas et al. ..... 359/345
6,847,448 B2 * 1/2005 Nagashima et al. ......... 356/364

OTHER PUBLICATIONS

Yasui et al., "Asynchronous optical sampling terahertz time-domain spectroscopy for ultrahigh spectral resolution and rapid data acquisition," 2005, Applied Physics Letters, vol. 87, pp. 061101-1-061101-3.*
Keilmann et al., "Time-domain mid-infrared frequency-comb spectrometer,", Jul. 1, 2004, Optics Letters, vol. 29. No. 13, pp. 1542-1544.*
"THz Time-Domain Spectroscopy Technology", by Xingning Zhang et al., *China Academic Journal Electronic Publishing House*, vol. 42, No. 7, Jul. 2005, pp. 35-38.
"High-Resolution THz Spectrometer with kHz Scan Rates", by A. Bartels, *Optics Express*, vol. 14, No. 1, Jan. 2006, pp. 430-437.

* cited by examiner

*Primary Examiner*—David P Porta
*Assistant Examiner*—Kiho Kim
(74) *Attorney, Agent, or Firm*—Westman, Champlin & Kelly, P.A.

(57) ABSTRACT

A method and an apparatus for measuring terahertz time-domain spectrum, which relate to the field of terahertz time-domain spectrum. The method comprises the steps of: generating a first pulse laser beam from a first femtosecond laser device at a preset repetition frequency to generate THz pulses; generating a second pulse laser beam from a second femtosecond laser device at the repetition frequency; measuring electric field intensities of the THz pulses at respective phase differences between the first pulse laser beam and the second pulse laser beam; and obtaining a THz time-domain spectroscopy by performing Fourier transformation of data representative of the electric field intensities. THz spectrum measured according to the method and apparatus improves spectroscopy resolution and provides a broader detection range.

16 Claims, 2 Drawing Sheets

METHOD AND APPARATUS FOR MEASURING TERAHERTZ TIME-DOMAIN SPECTROSCOPY

BACKGROUND OF THE INVENTION

The present application claims priority of Chinese patent application Serial No. 200610171670.5, filed Dec. 31, 2006, the content of which is hereby incorporated by reference in its entirety.

1. Field of the Invention

The present invention relates to a technology of measuring terahertz time-domain spectrum, and in particularly, to a method and an apparatus for measuring terahertz time-domain spectrum by using femtosecond pulsed laser to generate and detect the terahertz (hereinafter referred as "THz" for short) pulses.

2. Description of the Prior Art

As the technology of generation and detection of terahertz waves (whose waveband ranges from 0.05 THz to 50 THz, particularly electromagnetic waves ranges from 0.1 Thz to 10 THz) grows up, relevant technology and application research of terahertz waves develop rapidly. Terahertz time-domain spectroscopy technology is one of the most important technologies in terahertz-wave research. Terahertz reflection or transmission spectrum of a detected object can be obtained by terahertz time-domain spectroscopy technology, and then the spectrum obtained can be used for discriminating composition of the object, thereby the technology can be widely used in various applications such as quality detection, security inspection, antiterrorism and the likes.

Document 1 (ZHANG XingNing, etc., Terahertz Time-domain Spectroscopy Technology, LASER AND OPTO-ELECTRONICS DEVELOPMENT, July, 2005, p 35~38) discloses a terahertz time-domain spectroscopy measuring method which uses a femtosecond laser device to generate a femtosecond laser beam, and the generated femtosecond laser beam is divided into two beams. One beam acts as a pumping beam to activate the terahertz laser device to generate terahertz pulses, and the other one acts as a detecting beam incident on the terahertz laser detector to measure the terahertz electric field intensity of the detected beam at arrival. When the optical path difference between the two propagation paths is constant, the generated terahertz pulses corresponding to each laser pulse have a constant delay relative to the detecting pulses. Therefore, only one point of the terahertz pulses in the time axis is detected by the detecting pulses. Terahertz electric field intensity at different time point in the time axis can be detected by a set of precise mechanical displacement means which can adjusts the propagation path of one beam (usually the detecting beam) to change the propagation path difference there between, and then the time-domain waveform of the amplitude of the terahertz pulses can be obtained. After that, a spectrogram (time-domain spectroscopy) of the terahertz pulses can be obtained by performing Fourier transformation of the intensity data of the pulses.

However, such conventional terahertz time-domain spectroscopy method uses mechanical time-delay means. It is difficult to make measurement over a broad time window (for example, 1 ns or even larger than 1 ns) because movement of the mechanical means inevitably changes the path (including size of faculae, displacement of the position and so on), and the larger the movement is, the more the optical path changes, so the spectroscopy resolution thereof is limited (the typical value is 3-50 GHz). Furthermore, the scan speed of the system which is based on mechanical time-delay means is slow. In the case, the spectroscopy resolution has to be sacrificed in order to improve the scan speed.

Document 2 (A. Bartels, etc., High-resolution THz spectrometer with kHz scan rates, OPTICS EXPRESS, Vol. 14, NO. 1, p 430~437) discloses a THz time-domain spectroscopy method which is a time-domain spectroscopy method of asynchronous optical sampling. In the method of Document 2, two femtosecond laser devices operating at different repetition frequencies are used to generate two femtosecond laser beams. The two laser beams generated by the two laser devices are used as a pumping beam and a detecting beam respectively. Unlike the Document 1 in which the THz time-domain spectroscopy measuring method requires mechanical time-delay means to adjust the delay between the pumping pulses and the detecting pulses, in the method of Document 2, the delay between the pulses of the two beams is always changed because these two beams operate at different repetition frequencies. Let the repetition frequency of the pumping beam be f, the frequency difference between the two lasers be Δf, then the detecting pulses scan the THz pulses one time in a time window of 1/f. The signal noise ratio can be improved through repetition scans, and the time-domain waveform can be obtained finally. As such, a spectrogram of the terahertz pulses can be obtained by performing Fourier transformation of the pulse intensity data.

As described above, the THz time-domain spectroscopy method based on asynchronous optical sampling can omit the mechanical time-delay means, and efficiently eliminate the conflict between the scan speed and the spectroscopy resolution, thus the system can operate at a high scan speed (the typical time of a single scan is 0.1 ms, and the typical SNR of multiple scans is 60 dB@60 s) while have a high spectroscopy resolution (the typical value is 1 GHz). However, the method increases the repetition frequency of the femtosecond laser (typically, to 1 GHz from 80 MHz) in order to guarantee the measuring bandwidth and solve the frequency stability problem, which makes the spectroscopy resolution can not be further improved (the theoretical spectroscopy resolution of 1 GHz repetition frequency is 1 GHz). Moreover, in order to broader the detection bandwidth, the stability of the laser repetition frequency should be improved, but it is very difficult to further improve the stability of the laser repetition frequency.

SUMMARY OF THE INVENTION

In order to overcome the disadvantages of prior art, the present invention provides a new method and apparatus for measuring THz time-domain spectrum, which obtain the time delay between two beams by adjusting initial phase difference of the two beams emitted from two femtosecond laser devices operating at the same repetition frequency.

In an aspect of the present invention, there is provided a method for measuring THz time-domain spectrum comprising the steps of: emitting a first pulse laser beam from a first femtosecond laser device at a preset repetition frequency to generate THz pulses; emitting a second pulse laser beam from a second femtosecond laser device at the repetition frequency; measuring electric field intensities of the THz pulses at respective phase differences between the first pulse laser beam and the second pulse laser beam; and obtaining the THz time-domain spectrum by making Fourier transformation of data representative of the electric field intensities.

Furthermore, according to an embodiment of the present invention, the method further includes a step of controlling the first femtosecond laser device and the second femtosecond laser device to operate at the same repetition frequency by feedback adjustment.

Furthermore, according to an embodiment of the present invention, the controlling step includes a step of adjusting the phase difference of the phases of the first pulse laser beam and the second pulse laser beam to a preset phase difference by adjusting the cavity length of the first femtosecond laser device and/or the second femtosecond laser device.

Furthermore, according to an embodiment of the present invention, the method also includes a step of converting the phase difference to a time difference based on the repetition frequency.

In another aspect of the present invention, there is provided an apparatus for measuring THz time-domain spectrum comprising a first femtosecond laser device for emitting a first pulse laser beam at a preset repetition frequency, a second femtosecond laser device for emitting a second pulse laser beam at the repetition frequency, measuring means for measuring electric field intensities of the THz pulses at respective phase differences between the first pulse laser beam and the second pulse laser beam; and data processing means for obtaining the THz time-domain spectroscopy by performing Fourier transformation of data representative of the electric field intensities.

Furthermore, according to an embodiment of the present invention, the apparatus further includes frequency and phase control means for controlling the first femtosecond laser device and the second femtosecond laser device to operate at the same repetition frequency by feedback adjustment.

Furthermore, according to an embodiment of the present invention, the frequency and phase control means adjusts the phase difference of the phases of the first pulse laser beam and the second pulse laser beam to a preset phase difference by adjusting the cavity length of the first femtosecond laser device and/or the second femtosecond laser device.

Furthermore, according to an embodiment of the present invention, the data processing means converts the phase difference to a time difference based on the repetition frequency.

Furthermore, according to an embodiment of the present invention, each of the first and the second femtosecond laser devices comprises a continuous laser pumping source and a femtosecond oscillator.

Furthermore, according to an embodiment of the present invention, the continuous laser pumping source and the femtosecond oscillator are separated.

Furthermore, according to an embodiment of the present invention, the continuous laser pumping source and the femtosecond oscillator are integrated.

Furthermore, according to an embodiment of the present invention, the first and the second femtosecond laser device is provided with one and the same continuous laser pumping source.

Furthermore, according to an embodiment of the present invention, the first and the second femtosecond laser devices are provided with respective continuous laser pumping sources.

Furthermore, according to an embodiment of the present invention, the apparatus also includes a first beam splitter disposed at output of the first femtosecond laser device, for feeding the first pulse laser beam back; a first photodetector for converting the feedback first pulse laser beam to electrical signals as the feedback signals; a second beam splitter disposed at output of the second femtosecond laser device; a second photodetector for converting the feedback scond pulse laser beam to electrical signals as the feedback signals.

Furthermore, according to an embodiment of the present invention, the first beam splitter and the first photodetector are integrated in the first femtosecond laser device, and the second beam splitter and the second photodetector are integrated in the second femtosecond laser device.

Furthermore, according to an embodiment of the present invention, the first beam splitter and the first photodetector are separated from the first femtosecond laser, and the second beam splitter and the second photodetector are separated from the second femtosecond laser.

The present invention has the following advantages over prior art due to the method and apparatuses described above:

1. The path adjustment difficulty is lowered because there is no conventional mechanical time-delay means in the propagation path, and thus the measurement is speeded up.

2. In the present invention, the repetition frequency of the laser can be tens megahertz to several gigahertz. Therefore, users can make selection based on the requirement for spectroscopy resolution. For example, the highest spectroscopy resolution of the system can reach 80 MHz when the laser repetition frequency is 80 MHz.

3. Compared with prior art, THz spectroscopy measured according to the method and apparatus of present invention has a higher spectroscopy resolution and a broader detection range, which makes the technology of present invention have stronger capability for discriminating substances.

BRIEF DESCRIPTION OF THE DRAWINGS

The above and/or other aspects of the present invention will become apparent and more readily appreciated from the following description of the exemplary embodiments, taken in conjunction with the accompanying drawings, in which.

DETAILED DESCRIPTION OF THE INVENTION

Figure 1:
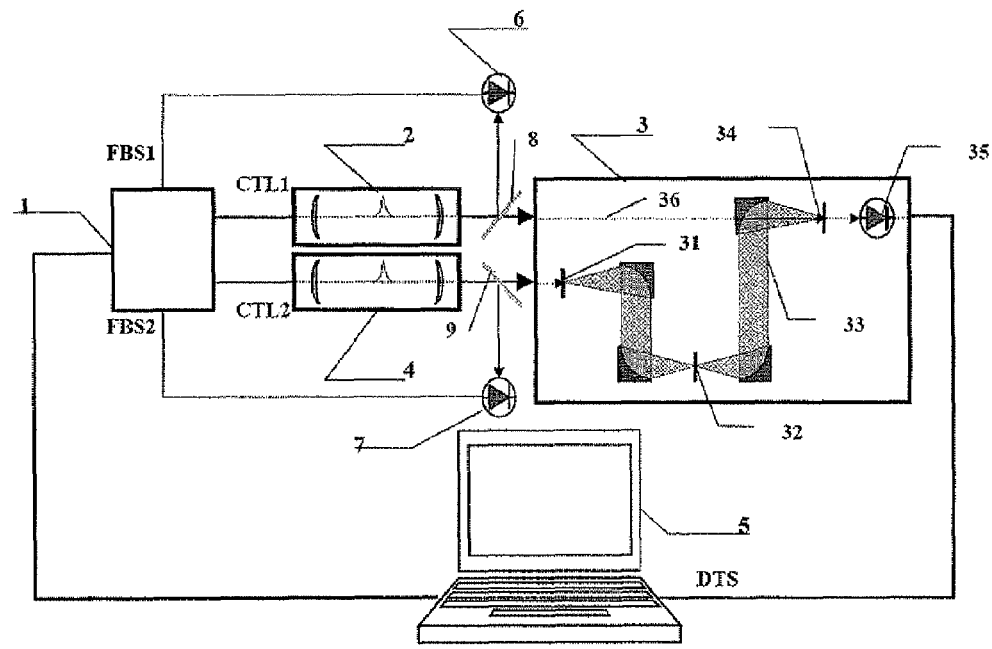
FIG. 1 is a block diagram of an apparatus for measuring THz time-domain spectroscopy according to an embodiment of the present invention.

Reference will now be made in detail to the embodiments of the present invention, examples of which are illustrated in the accompanying drawings, wherein like reference numerals refer to like elements throughout. The embodiments are described below to explain the present invention by referring to the figures.

FIG. 1 shows a block diagram of an apparatus for measuring THz time-domain spectrum according to an embodiment of the present invention. As shown in FIG. 1, the apparatus according to an embodiment of the present invention comprises two femtosecond laser devices 2 and 4 operating at the same repetition frequency, such as 100 MHz; a THz emission and detection component 3 which includes a THz emitter 31, a detection crystal 34, a photoelectric converter 35, a femtosecond laser optical path 36, a THZ optical path 33 and a sample stage for carrying a sample 32; two beam splitters 8 and 9; two photoelectric detectors 6 and 7; repetition frequency and phase control part 1 which stabilizes the repetition frequencies of the femtosecond laser devices 2 and 4 to a preset reference frequency based on signals fed back from the photoelectric detectors 6 and 7, and adjusts the phase difference between the beams emitted from the femtosecond laser devices 2 and 4 to a preset value at the same time; and a computer-based data collecting and processing system 5.

Here, the femtosecond laser device 2 or 4 includes a continuous laser pumping source and a femtosecond oscillator which are separated or integrated. In the discrete case, the two femtosecond oscillators can use either difference continuous laser pumping sources or one and the same continuous laser pumping source.

A sample 32 is placed on the THz propagation path, and various sample stages can be used. According to environmental quality, the sample stage may be a general test bench, and also may be an inclosed and dry control box. The beam splitters 8 and 9 and the photoelectric detector 6 and 7 can be integrated into the femtosecond laser devices 2 and 4 respectively so as to keep the propagation path stable.

As shown in FIG. 1, the repetition frequency and phase control part 1 accepts a control command issued from the data collecting and processing system 5, and controls the femtosecond lasers devices 2 and 4 to operate at the same repetition frequency, such as 100 MHz, and adjusts the phase difference between the laser beams emitted from the two femtosecond laser devices 2 and 4 at the same time. The femtosecond pulse laser beam emitted from the femtosecond laser device 4 acts as a pumping beam to activate the THz emitter 31 in the component 3 to emit THz pulses. The femtosecond pulse laser beam emitted from the femtosecond laser device 2 acts as a detecting beam incident on the detection crystal 34 in the component 3. That is to say, the THz pulses emitted from the THz emitter 31 interact with the sample 32, and then reach the detection crystal 34 along the THz propagation path 33. The detection crystal 34 detects instantaneous electric field intensities of the THz pulses at respective preset phase differences with the assist of the peripheral components such as the photoelectric converter 35. Specially, the detection crystal 34 changes the polarization of the laser beam emitted from the femtosecond laser device 2 with the effect of the THz electric field, and the photoelectric converter 35 measures the tiny change of the laser amplitude in the polarization to get a THz electric field intensity DTS in analog form, and then delivers it to the data collecting and processing system 5 via a data line. The data collecting and processing system 5 controls the entire apparatus to operate harmoniously, and obtains electric field intensity data of the THZ pulses at respective phase differences from the component 3, and performs Fourier transformation and process to get a THz time-domain spectrum.

Figure 2:
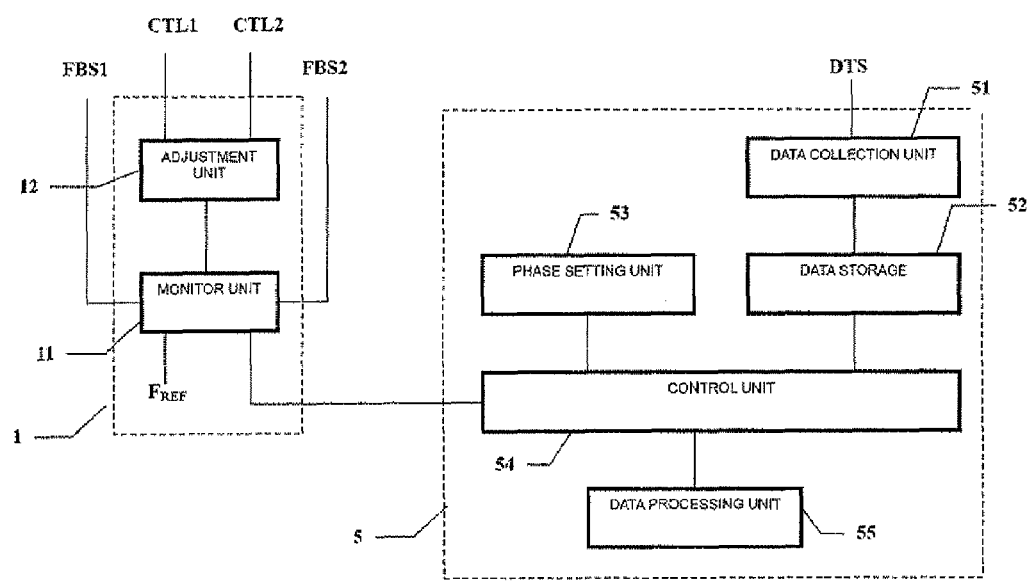
FIG. 2 is a detailed schematic diagram of some portions of the apparatus shown in FIG. 1.

FIG. 2 is a detailed schematic diagram of some portions of the apparatus shown in FIG. 1. As shown in FIG. 2, the data collecting and processing system comprises a data collection unit 51 which converts the THz electric field intensities denoted by analog signals DTS inputted from outside to digital data; a data storage 52 in which the digital data collected by the data collection unit 51 is stored; a phase setting unit 53 which presets several phases (phase differences), such as $\theta_1$, $\theta_2, \ldots, \theta_N$, according to inputs of a user, as an example, $\theta_1=0$, $\theta_2=2\times 2\pi/65536$, $\theta_3=3\times 2\pi/65536$, $\theta_N=65535\times 2\pi/65536$; a control unit 54 which issues a control command to the repetition frequency and phase control part 1 according to respective preset phase differences to stabilize the repetition frequency at the preset reference frequency, and instructs the repetition frequency and phase control part 1 to control the phase differences between the two laser beams at respective preset phase differences $\theta_i$ (i=1,2, ..., N), and instructs the data collection unit 51 to collect THz electric field intensity data Si (i=1,2, ..., N) at respective phase differences; and a data processing unit 55 which converts the phase differences $\theta_i$ read out from the data storage 52 by the control unit 54 into corresponding time differences $T_i$ (i=1,2, ..., N) after obtaining the THz electric field intensities $F_i$ at respective phase differences $\theta_i$, and performs Fourier transformation of the THz electric field intensities $F_i$ (i=1,2, ..., N) to obtain the time-domain spectroscopy of the THz pulses. Here, a time length of a $2\pi$ period corresponding to the repetition frequency can be obtained because the repetition frequency has been known. Therefore, the above phase differences $\theta_i$ and the converted time differences $T_i$ (i=1,2, ..., N) are in one to one correspondence.

As shown in FIG. 2, the repetition frequency and phase control part 1 comprises a monitor unit 11 which issues to an adjustment unit 12 instructions CTL1 or CTL 2, according to a reference signal $F_{REF}$, the phase differences supplied by the control unit 54, a feedback signal FBS1 from the photoelectric detector 6 and a feedback signal FBS2 from the photoelectric detector 6, instructs the adjustment unit 12 to adjust the cavity length of the femtosecond laser device 2 or 4 by means of, for example, piezoelectricity, so as to make the repetition frequency of the laser pulses emitted from the femtosecond laser devices 2 and 4 same as the reference frequency, and the phase difference therebetween same as the phase difference $\theta_i$ supplied by the control unit. In the case, the data collection unit 51 obtains the THz electric field data $S_i$ at the phase difference $\theta_i$. And then, the above operation is repeated to obtain THz electric field intensities at respective phase differences.

Figure 3:
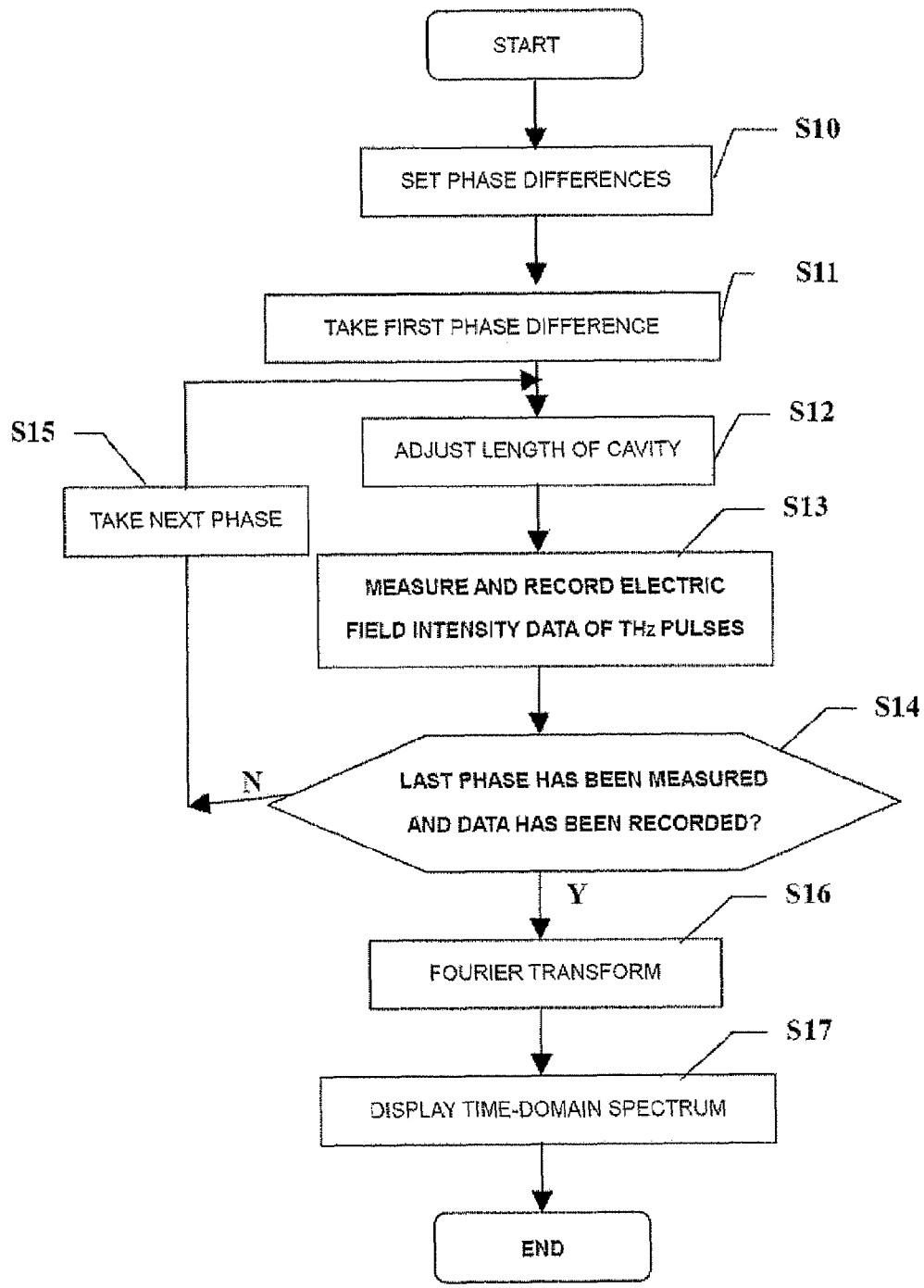
FIG. 3 is a flowchart of a method for measuring THz time-domain spectrum according to an embodiment of the present invention.

FIG. 3 shows a flowchart of a method for measuring THz time-domain spectroscopy according to an embodiment of the present invention.

As shown in FIG. 3, a user sets several phase differences by means of the phase setting unit 53 in the data collecting and processing system S. For example, if a range of the preset phases, such as $0\sim 2\pi$, and a division number N=65536 are selected, then respective phase differences $\theta_1, \theta_2, \ldots, \theta_N$ are determined (S10).

After that, take the first phase difference $\theta_1$ to make measurement (S11). The monitor unit 11 issues instructions CTL1 or CTL 2 to the adjustment unit 12, according to the reference FREF, the phase differences supplied by the control unit 54, a feedback signal FBS1 from the photoelectric detector 6 and a feedback signal FBS2 from the photoelectric detector 6, instructs the adjustment unit 12 to adjust the cavity length of the femtosecond laser device 2 or 4 by means of, for example, piezoelectricity, so as to make the repetition frequency of the laser pulses emitted from the femtosecond laser devices 2 and 4 same as the reference frequency, and the phase difference therebetween same as the phase difference $\theta_i$ supplied by the control unit (S12).

Then, the detection crystal 34 detects instantaneous electric field intensity of the THz pulses at the phase difference with the assist of the peripheral components such as the photoelectric converter 35. After that, the data collection unit 51 converts the THz electric field intensity signal DTS of analog data into digital data, and stores it in the data storage 52 (S13).

In the next, the control unit 54 determines whether all the preset phase differences have been measured (S14). If not, then the control unit 54 takes the next phase difference (S15), and the flow returns to step S11 to repeat the same processing procedure as above.

If all the phase differences have been measured (YES at S14), then the control unit 54 reads the phase differences $\theta_i$ out from the data storage 52, converts them into corresponding time differences $T_i$ (i=1, 2, ... N), and transmits them to the data processing unit 54. Hereafter, the data processing unit 55 performs Fourier transformation of the THz electric field intensities $F_i$ (i=1,2, ..., N) to obtain time-domain spectroscopy of the THz pulses (S16). Finally, the obtained time-domain spectroscopy is displayed on the screen or printed out (S17).

As stated above, because the repetition frequency has been known, it is easy to compute a time length of $2\pi$ period corresponding to the repetition frequency. Therefore, the above phase differences $\theta_i$ and the converted time differences $T_i$ (i=1,2, ..., N) are in one to one correspondence. Furthermore, though in the above description, the THz electric field intensity is measured in a time interval of $0\sim 2\pi$, a certain preset range can be set, such as a time interval of $0\sim\pi$ or a segment thereof (such as a range centered at the peak value).

Although the exemplary embodiments of the present invention have been shown and described, it will be appreciated by those skilled in the art that changes may be made in these embodiments without departing from the principles and spirit of the invention, the scope of which is defined in the appended claims and their equivalents.

What is claimed is:

1. A method for measuring THz time-domain spectrum comprising the steps of:

emitting a first pulse laser beam from a first femtosecond laser device at a preset repetition frequency to excite a THz emitter to generate THz pulses, wherein the THz pulses interact with a sample to be tested before being incident on a detection device;

emitting a second pulse laser beam from a second femtosecond laser device at the repetition frequency, the second pulse laser beam triggering the detection device;

controlling the first femtosecond laser device and the second femtosecond laser device so that the first pulse laser beam and the second pulse laser beam emitted therefrom respectively have a varying phase difference therebetween, measuring, by the detection device, electric field intensities of the THz pulses at respective phase differences between the first pulse laser beam and the second pulse laser beam; and obtaining a THz time-domain spectrum by performing Fourier transformation of data representative of the electric field intensities.

2. The method according to claim 1, further comprising a step of:

controlling the first femtosecond laser device and the second femtosecond laser device to operate at the same repetition frequency by feedback adjustment.

3. The method according to claim 2, further comprising a step of:

adjusting the phase difference of the phases of the first pulse laser beam and the second pulse laser beam to a preset phase difference by adjusting the cavity length of the first femtosecond laser device and/or the second femtosecond laser device.

4. The method according to claim 1, further comprising a step of:

converting the phase difference to a time difference based on the repetition frequency.

5. An apparatus for measuring THz time-domain spectrum comprising:

a first femtosecond laser device for emitting a first pulse laser beam at a preset repetition frequency to excite a THz emitter to generate THz pulses, wherein the THz pulses interact with a sample to be tested before being incident on a detection device;

a second femtosecond laser device for emitting a second pulse laser beam at the repetition frequency, the second pulse laser beam triggering the detection device;

a control device for controlling the first femtosecond laser device and the second femtosecond laser device so that the first pulse laser beam and the second pulse laser beam emitted therefrom respectively have a varying phase difference therebetween, the detection device for measuring electric field intensities of the THz pulses at respective phase differences between the first pulse laser beam and the second pulse laser beam; and data processing means for obtaining the THz time-domain spectroscopy by performing Fourier transformation of data representative of the electric field intensities.

6. The apparatus according to claim 5, wherein the control device controls the first femtosecond laser device and the second femtosecond laser device to operate at the same repetition frequency by feedback adjustment.

7. The apparatus according to claim 6, wherein the control device adjusts the phase difference of the phases of the first pulse laser beam and the second pulse laser beam to a preset phase difference by adjusting the cavity length of the first femtosecond laser device and/or the second femtosecond laser device.

8. The apparatus according to claim 6, further comprising:

a first beam splitter disposed at output of the first femtosecond laser device, for feeding the first pulse laser beam back;

a first photodetector for converting the feedback first pulse laser beam to electrical signals as the feedback signals;

a second beam splitter disposed at output of the second femtosecond laser device;

a second photodetector for converting the feedback second pulse laser beam to electrical signals as the feedback signals.

9. The apparatus according to claim 8, wherein the first beam splitter and the first photodetector are integrated in the first femtosecond laser device, and the second beam splitter and the second photodetector are integrated in the second femtosecond laser device.

10. The apparatus according to claim 8, wherein the first beam splitter and the first photodetector are separated from the first femtosecond laser, and the second beam splitter and the second photodetector are separated from the second femtosecond laser.

11. The apparatus according to claim 5, wherein
the data processing means converts the phase difference to a time difference based on the repetition frequency.

12. The apparatus according to claim 5, wherein
each of the first and the second femtosecond laser devices comprises a continuous laser pumping source and a femtosecond oscillator.

13. The apparatus according to claim 12, wherein the continuous laser pumping source and the femtosecond oscillator are separated.

14. The apparatus according to claim 13, wherein the first and the second femtosecond laser devices are provided with one and the same continuous laser pumping source.

15. The apparatus according to claim 13, wherein the first and the second femtosecond laser devices are provided with respective continuous laser pumping sources.

16. The apparatus according to claim 12, wherein the continuous laser pumping source and the femtosecond oscillator are integrated.

* * * * *